and al.(12) United States Patent
Krull et al.

(10) Patent No.: US 9,039,870 B2
(45) Date of Patent: *May 26, 2015

(54) METHOD FOR PRODUCING ALKALINE (METH)ACRYLAMIDES

(75) Inventors: Matthias Krull, Harxheim (DE); Christoph Kayser, Mainz (DE); Roman Morschhaeuser, Mainz (DE); Helmut Ritter, Wuppertal (DE); Sarah Schmitz, Duesseldorf (DE)

(73) Assignee: Clariant Finance (BVI) Limited, Tortola (VG)

( * ) Notice: Subject to any disclaimer, the term of this patent is extended or adjusted under 35 U.S.C. 154(b) by 400 days.

This patent is subject to a terminal disclaimer.

(21) Appl. No.: 12/444,678

(22) PCT Filed: Oct. 5, 2007

(86) PCT No.: PCT/EP2007/008677
§ 371 (c)(1),
(2), (4) Date: Apr. 7, 2009

(87) PCT Pub. No.: WO2008/043492
PCT Pub. Date: Apr. 17, 2008

(65) Prior Publication Data
US 2010/0032284 A1 Feb. 11, 2010

(30) Foreign Application Priority Data
Oct. 9, 2006 (DE) .................... 10 2006 047 617

(51) Int. Cl.
*B01J 19/12* (2006.01)
*C07C 231/02* (2006.01)
*C07D 213/75* (2006.01)
*C07D 249/08* (2006.01)

(52) U.S. Cl.
CPC ............ *C07C 231/02* (2013.01); *B01J 19/126* (2013.01); *C07D 213/75* (2013.01); *C07D 249/08* (2013.01)

(58) Field of Classification Search
CPC ... C07C 231/02; B01J 19/126; C07D 249/08; C07D 213/75
USPC ............ 204/157.82, 157.87, 157.89; 528/422
See application file for complete search history.

(56) References Cited

U.S. PATENT DOCUMENTS

| | | | |
|---|---|---|---|
| 1,972,142 A * | 9/1934 | Goldstein | 552/266 |
| 2,601,561 A | 6/1952 | Schertz | |
| 3,024,260 A | 3/1962 | Ernst | |
| 3,050,418 A | 8/1962 | Mendelsohn et al. | |
| 3,113,026 A | 12/1963 | Sprung | |
| 3,197,473 A * | 7/1965 | Klosa | 546/276.1 |
| 3,395,162 A | 7/1968 | Lamberti | |
| 3,585,224 A | 6/1971 | Friedrich et al. | |
| 3,652,434 A | 3/1972 | Bar-Nun et al. | |
| 3,652,671 A | 3/1972 | Barron | |
| 3,682,946 A | 8/1972 | Liechti | |
| 3,836,551 A | 9/1974 | Schroeder et al. | |
| 4,133,833 A | 1/1979 | Hull | |
| 4,165,311 A | 8/1979 | Isowa et al. | |
| 4,221,948 A | 9/1980 | Jean | |
| 4,339,648 A | 7/1982 | Jean | |
| 4,582,933 A | 4/1986 | Mertens et al. | |
| 4,675,319 A * | 6/1987 | Nardi et al. | 514/235.8 |
| 4,859,796 A * | 8/1989 | Hurtel et al. | 564/204 |
| 4,994,541 A | 2/1991 | Dell et al. | |
| 5,114,684 A | 5/1992 | Walker | |
| 5,185,466 A * | 2/1993 | Kozulic et al. | 564/208 |
| 5,304,766 A | 4/1994 | Baudet et al. | |
| 5,326,538 A | 7/1994 | Walker | |
| 5,387,397 A * | 2/1995 | Strauss et al. | 422/186 |
| 5,419,815 A | 5/1995 | Doerpinghaus et al. | |
| 5,646,318 A | 7/1997 | Dery et al. | |
| 5,646,319 A | 7/1997 | Letton et al. | |
| 5,710,295 A | 1/1998 | Woodbury et al. | |
| 5,830,953 A | 11/1998 | Nishikawa et al. | |
| 5,856,538 A | 1/1999 | Strecker et al. | |
| 5,866,531 A | 2/1999 | Assmann et al. | |
| 5,892,115 A | 4/1999 | Aizawa et al. | |
| 5,988,877 A | 11/1999 | Hochrad et al. | |
| 6,017,426 A | 1/2000 | Semeria et al. | |

(Continued)

FOREIGN PATENT DOCUMENTS

| | | |
|---|---|---|
| CH | 681586 | 4/1993 |
| CN | 1228910 | 9/1999 |

(Continued)

OTHER PUBLICATIONS

Kumar, et al., "Microwave Assisted Direct Synthesis of 2-Substituted Benzoxazoles From Carboxylic Acids Under Catalyst and Solvent-Free Conditions", Synlett, No. 9, 2005, pp. 1401-1404.
"Microwave Synthesis" by B. L. Hayes, CEM Publishing 2002.
Goretzki et al., Macromol. Rapid Commun. 2004, 25, 513-516.
Gelens et al., Tetrahedron Letters 2005, 46(21), 3751-3754.
M. S. Nery, et al., "Niobium pentachloride promoted conversion of carboxylic acids to carboxamides: Synthesis of the 4-aryl-$1_1$2,3,4-tetrahydrolsoquinollne alkaloid structures" Synthesis, (2),272-276, 2003.
Vazquez-Tato, M.P., "Microwave-Mediated Synthesis of Amides", Synlett, No. 7, 1993, p. 506.
X. Wu, et al., "Microwave Enhanced Aminocarbonylations in Water", Organic Letters, 7(15), pp. 3327-3329, 2005.

(Continued)

*Primary Examiner* — Colleen M Raphael
(74) *Attorney, Agent, or Firm* — Tod A. Waldrop

(57) ABSTRACT

The invention relates to a method for producing alkaline amides or imides of ethylenically unsaturated $C_3$ to $C_6$ carboxylic acids by reacting amines that contain at least one primary and/or secondary amino group and at least one tertiary amino group with ethylenically unsaturated $C_3$ to $C_6$ carboxlic acids to form an ammonium salt and said ammonium salt is subsequently converted into the alkaline amide or imide by means of microwave radiation, with the proviso that the primary and/or secondary amino group is devoid of alkoxy groups.

19 Claims, No Drawings

(56) References Cited

U.S. PATENT DOCUMENTS

| | | | |
|---|---|---|---|
| 6,107,498 A * | 8/2000 | Maisonneuve et al. | 554/69 |
| 6,120,741 A | 9/2000 | Jacquault et al. | |
| 6,121,471 A * | 9/2000 | Scott | 554/69 |
| 6,127,560 A | 10/2000 | Stidham et al. | |
| 6,175,037 B1 | 1/2001 | Tweedy | |
| 6,291,712 B1 | 9/2001 | Saihata et al. | |
| 6,319,187 B1 * | 11/2001 | Scott | 546/187 |
| 6,365,885 B1 | 4/2002 | Roy et al. | |
| 6,373,040 B2 | 4/2002 | Thomas | |
| 6,614,010 B2 | 9/2003 | Fagrell et al. | |
| 6,794,510 B2 | 9/2004 | Le Bourdonnec et al. | |
| 6,867,400 B2 | 3/2005 | Collins et al. | |
| 6,960,627 B2 | 11/2005 | Huth et al. | |
| 6,989,519 B2 * | 1/2006 | Collins et al. | 219/679 |
| 7,098,351 B2 * | 8/2006 | Hoong et al. | 554/69 |
| 7,150,836 B2 | 12/2006 | Meikrantz | |
| 7,393,920 B2 | 7/2008 | Collins et al. | |
| 7,473,739 B2 | 1/2009 | Dairoku et al. | |
| 7,759,454 B2 | 7/2010 | Falk et al. | |
| 2003/0021793 A1 | 1/2003 | Hilgers | |
| 2005/0027120 A1 | 2/2005 | Gojon-Zorrilla | |
| 2005/0272631 A1 | 12/2005 | Miracle et al. | |
| 2005/0274065 A1 | 12/2005 | Portnoff et al. | |
| 2005/0283011 A1 | 12/2005 | Hoong et al. | |
| 2006/0057482 A1 | 3/2006 | Yuasa | |
| 2006/0228088 A1 | 10/2006 | Charlier de Chily et al. | |
| 2006/0252884 A1 * | 11/2006 | Falk et al. | 525/86 |
| 2006/0291827 A1 | 12/2006 | Suib et al. | |
| 2007/0049721 A1 | 3/2007 | Nefzger et al. | |
| 2007/0060762 A1 | 3/2007 | Kawashima et al. | |
| 2008/0009541 A1 | 1/2008 | Chambers et al. | |
| 2008/0202982 A1 | 8/2008 | Tooley | |
| 2008/0264934 A1 | 10/2008 | Moreira et al. | |
| 2010/0010244 A1 | 1/2010 | Krull et al. | |
| 2010/0076040 A1 | 3/2010 | Krull et al. | |
| 2010/0081843 A1 | 4/2010 | Krull et al. | |
| 2010/0116642 A1 | 5/2010 | Krull et al. | |
| 2010/0173107 A1 | 7/2010 | Hahn et al. | |
| 2011/0083956 A1 | 4/2011 | Krull et al. | |
| 2011/0083957 A1 | 4/2011 | Krull et al. | |
| 2011/0089019 A1 | 4/2011 | Krull et al. | |
| 2011/0089020 A1 | 4/2011 | Krull et al. | |
| 2011/0089021 A1 | 4/2011 | Krull et al. | |
| 2011/0092722 A1 | 4/2011 | Krull et al. | |
| 2011/0137081 A1 | 6/2011 | Krull et al. | |
| 2012/0088885 A1 | 4/2012 | Krull et al. | |
| 2012/0088918 A1 | 4/2012 | Krull et al. | |
| 2012/0090983 A1 | 4/2012 | Krull et al. | |
| 2012/0095220 A1 | 4/2012 | Krull et al. | |
| 2012/0095238 A1 | 4/2012 | Krull et al. | |
| 2012/0103790 A1 | 5/2012 | Krull et al. | |
| 2012/0178951 A1 | 7/2012 | Krull et al. | |
| 2012/0184758 A1 | 7/2012 | Krull et al. | |
| 2013/0274368 A1 | 10/2013 | Krull et al. | |
| 2013/0289206 A1 | 10/2013 | Krull et al. | |
| 2013/0296457 A1 | 11/2013 | Krull et al. | |
| 2013/0296458 A1 | 11/2013 | Krull et al. | |
| 2014/0200312 A1 | 7/2014 | Krull et al. | |

FOREIGN PATENT DOCUMENTS

| | | |
|---|---|---|
| CN | 1351954 | 6/2002 |
| CN | 1749279 | 3/2006 |
| CN | 1931980 | 3/2007 |
| DE | 480866 | 8/1929 |
| DE | 1139738 | 11/1962 |
| DE | 2009156 | 7/1970 |
| DE | 2620638 | 11/1977 |
| DE | 3209800 | 9/1983 |
| DE | 224203 | 7/1985 |
| DE | 102005051637 | 5/2007 |
| DE | 102006047619 | 5/2010 |
| DE | 102009001382 | 9/2010 |
| EP | 0134995 | 3/1985 |
| EP | 0207901 | 1/1987 |
| EP | 0226501 | 6/1987 |
| EP | 0383605 | 8/1990 |
| EP | 0437480 | 7/1991 |
| EP | 0722994 | 7/1996 |
| EP | 0377177 | 7/1997 |
| EP | 0884305 | 12/1998 |
| EP | 1256565 | 11/2002 |
| EP | 1291077 | 3/2003 |
| EP | 1435364 | 7/2004 |
| EP | 1491552 | 12/2004 |
| EP | 1712543 | 10/2006 |
| EP | 1775311 | 4/2007 |
| EP | 2079762 | 6/2007 |
| EP | 1849854 | 10/2007 |
| EP | 1884559 | 2/2008 |
| GB | 0385978 | 3/1931 |
| GB | 0414366 | 7/1934 |
| GB | 0719792 | 12/1954 |
| GB | 2094806 | 9/1982 |
| GB | 2095262 | 9/1982 |
| GB | 2361918 | 11/2001 |
| JP | 10330338 | 5/1997 |
| JP | 11508873 | 8/1999 |
| JP | 2003321427 | 11/2003 |
| JP | 2005322582 | 5/2004 |
| JP | 2006181533 | 12/2004 |
| JP | 2005060256 | 3/2005 |
| JP | 2006272055 | 3/2005 |
| JP | 2008031082 | 2/2008 |
| JP | 2009263497 | 11/2009 |
| WO | WO 90/03840 | 4/1990 |
| WO | WO 94/18243 | 8/1994 |
| WO | WO 95/06518 | 3/1995 |
| WO | WO 95/09821 | 4/1995 |
| WO | WO 96/14344 | 5/1996 |
| WO | WO 98/29461 | 7/1998 |
| WO | WO 98/29467 | 7/1998 |
| WO | WO 98/39370 | 9/1998 |
| WO | WO 03/014272 | 2/2003 |
| WO | WO 03/016359 | 2/2003 |
| WO | WO 03/041856 | 5/2003 |
| WO | WO 03/090669 | 11/2003 |
| WO | WO 2004/054707 | 7/2004 |
| WO | WO2004/072031 | 8/2004 |
| WO | WO2005/033062 | 4/2005 |
| WO | WO2005/118526 | 12/2005 |
| WO | WO 2006/024167 | 3/2006 |
| WO | WO 2007/065681 | 6/2007 |
| WO | WO 2007/110384 | 10/2007 |
| WO | WO 2007/126166 | 11/2007 |
| WO | WO 2008/043492 | 4/2008 |
| WO | WO 2008/043493 | 4/2008 |
| WO | WO 2008/043494 | 4/2008 |
| WO | WO 2008/043495 | 4/2008 |
| WO | WO 2009/002880 | 12/2008 |
| WO | WO 2009/064501 | 5/2009 |
| WO | WO 2009/121490 | 10/2009 |

OTHER PUBLICATIONS

Massicot et al., Synthesis 2001 (16), 2441-2444.
Iannelli et al., Tetrahedron 2005, 61, 1509-1515.
R. Martinez-Palou, et al., "Synthesis of Long Chain 2-Alkyl-1-(2-hydroxyethyl)-2-imidazolines Under Microwave in Solvent-Free Conditions", Synlett 2003, No. 12, pp. 1847-1849.
R. Plantier-Royon, et al., "Synthesis of Functionalized Bis-Amides of L-(+)-Tartaric Acid and Application as Copper(II) Ligands", C.R. Chimie, 2004, pp. 119-123.
R.S. Hunter, "Conversion of Visual to Instrumental Measurements of Yellowness", 1981, JAOCS, May, pp. 606-612.
Synthewave 402 Manual, 2000, Prolabo, Support pp. 2 and Manual pp. 1-13 (total 15 pages).
Beilstein Substance Identification, BRN No. 6190607, 1981.
S. Schmitz, et al., "Access to Poly{N-[3-(dimethylamino)propyl](meth)acrylamide} via Microwave-Assisted Synthesis and Control of LCST-Behavior in Water", Macromolecular Rapid Communications, vol. 28, No. 21, Nov. 1, 2007, pp. 2080-2083.

(56) References Cited

OTHER PUBLICATIONS

English Abstract of JP52125142, Oct. 20, 1977.
English Abstract of JP54005931, Jan. 17, 1979.
English Abstract of DD224203, Jul. 3, 1985.
H.J. Bauer, et al., Makromol. Chem., 183, 1982, pp. 2971-2976.
International Search Report for PCT/EP2007/008677 Mail dated Mar. 3, 2008.
Translation of International Preliminary Report on Patentability for PCT/EP2007/008677, Mar. 3, 2008.
International Search Report for PCT/EP2007/008678 Mail dated Mar. 10, 2008.
Translation of International Preliminary Report on Patentability for PCT/EP2007/008678, Mar. 10, 2008.
International Search Report for PCT/EP2007/008679 Mail dated Feb. 4, 2008.
International Search Report for PCT/EP2007/008680 Mail dated Feb. 15, 2008.
Translation of International Preliminary Report on Patentability for PCT/EP2007/008680, Feb. 15, 2008.
International Search Report for PCT/EP2007/008681 Mail dated Jan. 29, 2008.
Translation of International Preliminary Report on Patentability for PCT/EP2007/008681, Jan. 29, 2008.
International Search Report for PCT/EP2009/001989 mail dated Jun. 10, 2009.
Translation of International Preliminary Report on Patentability for PCT/EP2009/001989, dated Oct. 14, 2010.
International Search Report for PCT/EP2009/001985 mail dated Jun. 10, 2009.
Translation of International Preliminary Report on Patentability for PCT/EP2009/001985, dated Oct. 14, 2010.
International Search Report for PCT/EP2009/001986 mail dated Jun. 18, 2009.
Translation of International Preliminary Report on Patentability for PCT/EP2009/001986, dated Oct. 14, 2010.
International Search Report for PCT/EP2009/001987 mail dated Jun. 10, 2009.
Translation of International Preliminary Report on Patentability for PCT/EP2009/001987, dated Oct. 14, 2010.
International Search Report for PCT/EP2009/001984 mail dated Jun. 10, 2009.
Translation of International Preliminary Report on Patentability for PCT/EP2009/001984, dated Oct. 14, 2010.
International Search Report for PCT/EP2009/001990 mail dated Jun. 10, 2009.
Translation of International Preliminary Report on Patentability for PCT/EP2009/001990, dated Dec. 9, 2010.
International Search Report for PCT/EP2009/001988 mail dated Jul. 9, 2009.
Translation of International Preliminary Report on Patentability for PCT/EP2009/001988, dated Jan. 27, 2011.
International Search Report for PCT/EP2010/003443 mail dated Feb. 9, 2011.
Translation of International Preliminary Report on Patentability for PCT/EP2010/003443, dated Feb. 16, 2012.
International Search Report for PCT/EP2010/003442 mail dated Jul. 20, 2010.
Translation of International Preliminary Report on Patentability for PCT/EP2010/003442, dated Feb. 16, 2012.
International Search Report for PCT/EP2010/003445 mail dated Sep. 1, 2010.
Translation of International Preliminary Report on Patentability for PCT/EP2010/003445, dated Jan. 5, 2012.
International Search Report for PCT/EP2010/003444 mail dated Feb. 9, 2011.
Translation of International Preliminary Report on Patentability for PCT/EP2010/003444, dated Jan. 19, 2012.
Response to the Wriiten Opinion in PCT/EP2010/003444, dated Sep. 9, 2011.
International Search Report for PCT/EP2010/003447 mail dated Feb. 9, 2011.
Translation of International Preliminary Report on Patentability for PCT/EP2010/003447, dated Feb. 9, 2012.
Written Opinion of the IPEA for PCT/EP2010/003447, dated Sep. 9, 2011.
International Search Report for PCT/EP2010/003446 mail dated Feb. 9, 2011.
Translation of International Preliminary Report on Patentability for PCT/EP2010/003446, dated Jan. 19, 2012.
T. Cablewski, et al: "Development and Application of a Continuous Microwave Reactor for Organic Synthesis" Journal of Organic Chemistry, American Chemical Society, Easton.; US, vol. 59, Jan. 1, 1994, pp. 3408-3412, XP000198783.
Glasnov, et al: "Microwave-assisted synthesis under continuous-flow conditions", Macromolecular Rapid Communications, 28(4), 395-410 CODEN: MRCOE3; Jan. 1, 2007, XP002529633.
L. Perreux, et al: "Solvent-free preparation of amides from acids and primary amines under microwave irradiation", Tetrahedron, Elsevier Science Publishers, Amsterdam, NL, vol. 58, No. 11, Mar. 11, 2002, pp. 2155-2162, XP004343866.
C. Ferroud, et al: "Microwaves-assisted solvent-free synthesis of N-acetamides by amidation or aminolysis", Tetrahedron Letters., vol. 49, Mar. 6, 2008, pp. 3004-3008, XP022602751 NL Elsevier, Amsterdam.
B. Toukoniitty, et al: "Esterification of propionic acid under microwave irradiation over an ion-exchange resin", Catalysis Today, Elsevier, NL, vol. 100, No. 3-4, Feb. 28, 2005, pp. 431-435, XP004850051.
Chemat, et al: "The role of selective heating in the microwave activation of heterogeneous catalysis reactions using a continuous microwave reactor", Journal of Microwave Power and Electromagnetic Energy, The Institute, Vienna, VA, US, vol. 33, No. 2, Jan. 1, 1998, pp. 88-94, XP009143773.
Konrad G, Kabza, et al: "Microwave-Induced Esterification Using Heterogeneous Acid Catalyst in a Low Dielectric Constant Medium", Journal of Organic Chemistry, American Chemical Society, Easton.; US, vol. 65, Jan. 1, 2000, pp. 1210-1214, XP007916930.
Erik Esveld, et al: "Pilot Scale Continuous Microwave Dry-Media Reactor. Part 1: Design and Modeling", Chemical Engineering and Technology, Weinheim, DE, vol. 23, No. 3, Jan. 1, 2000, pp. 279-283, XP007916923.
Erik Esveld, et al: "Pilot Scale Continuous Microwave Dry-Media Reactor Part II: Application to Waxy Esters Production", Chemical Engineering and Technology, Weinheim, DE, vol. 23, No. 5, Jan. 1, 2000, pp. 429-435, XP007916803.
Noel S. Wilson, et al: "Development and Applications of a Practical Continuous Flow Microwave Cell", Organic Process Research and Development, American Chemical Society, US, vol. 8, No. 3, Jan. 1, 2004, pp. 535-538, XP007916928.
G. Pipus, et al: "Esterification of benzoic acid in microwave tubular flow reactor", Chemical Engineering Journal, Elsevier Sequoia, Lausanne, CH, vol. 76, Jan. 1, 2000, pp. 239-245, XP007916929.
L. Perreux, et al: "Microwave effects in solvent-free esters aminolysis" Tetrahedron, Elsevier Science Publishers, Amsterdam, NL, vol. 59, No. 12, Mar. 17, 2003, pp. 2185-2189, XP004414169.
R. S. Varma, et al: "Solvent-free synthesis of amides from non-enolizable esters and amines using microwave irradiation" Tetrahedron Letters, Elsevier, Amsterdam, NL, vol. 40, No. 34, Aug. 20, 1999, pp. 6177-6180, XP004174006.
R. Jachuck, et al: "Process intensification: oxidation of benzyl alcohol using a continuous isothermal reactor under microwave irradiation", Green Chemistry, Royal Society of Chemistry, Cambridge, GB, vol. 8, Jan. 1, 2006, pp. 29-33, XP007916789.
English Abstract of EP1291077, Mar. 12, 2003.
J. Ruhoff, et al., J. Am. Chem. Soc., 59 (1937), 401-402.
C. Chen et al., J. Chem. Soc., Chem. Commun., 1990, 807-809.
Katritzky et al. (Energy & Fuels 4 (1990), 555-561).
An et al. (J. Org. Chem. (1997), 62, 2505-2511).
Pipus et al. (First European Congress on Chemical Engineering, Firenze, Italy, May 4-7, 1997; AIDIC: Milan, Italy, 1997; pp. 45-48).
Amore et al. (Macromolecular Rapid Communications, vol. 28 (2007), Issue 4, pp. 473-477).

(56) References Cited

OTHER PUBLICATIONS

Q. Yang et al. (Synth. Commun. 2008, 38, 4107-4115).
Zradni et al. (Synth. Commun. 2002, 32, 3525-3531).
J. Kremsner, et al, Top Curr Chem, (2006) 266: pp. 233-278.
Energieeintrag im Discover, "Flexibilitaet ist Trumpf", http://www.cem.de/documents/produlde/mikro_synthese/allgemeines/flexibel.htm, Jun. 2009.
D. Bogdal, Microwave-assisted Organic Synthesis, Elsevier 2005.
K. Lange, K.H. Löcherer, Taschenbuch der Hochfrequenztechnik [Pocket book of high-frequency technology], vol. 2, p. K21 ff.
"Microwave vs. Conventional Heating", webpage, www.biotage.com, Jan. 2009.
"Amide", Wikipedia, pp. 1-6, Jun. 20, 2012, (http://en.wikipedia.org/wiki/Amide).
International Search Report for PCT/EP2010/005427 dated Mar. 21, 2011.
Translation of International Preliminary Report on Patentability for PCT/EP2010/005427, dated Mar. 21, 2011.
International Search Report for PCT/EP2010/005428 dated Jan. 27, 2011.
Translation of International Preliminary Report on Patentability for PCT/EP2010/005428, dated Jan. 27, 2011.
International Search Report for PCT/EP2011/006173 mail dated May 8, 2012.
Translation of International Preliminary Report on Patentability for PCT/EP2011/006173, dated Jul. 4, 2013.
International Search Report for PCT/EP2011/006172 mail dated Jul. 10, 2012.
Translation of International Preliminary Report on Patentability for PCT/EP2011/006172, dated Jul. 4, 2013.
International Search Report for PCT/EP2011/006175 mail dated May 9, 2012.
Translation of International Preliminary Report on Patentability for PCT/EP2011/006175, dated Jul. 4, 2013.
International Search Report for PCT/EP2011/006174 mail dated Jul. 10, 2012.
Translation of International Preliminary Report on Patentability for PCT/EP2011/006174, dated Jul. 4, 2013.
International Search Report for PCT/EP2011/006176 mail dated Aug. 1, 2012.
Translation of International Preliminary Report on Patentability for PCT/EP2011/006176, dated Jul. 4, 2013.
"Objective Colour Assesment and Quality Control in the Chemical, Pharmaceutical and Cosmetic Industries", Application Report No. 3.9 e from Hach Lange, pp. 1-28, Feb. 2013.
(Hawley's Condensed Chemical Dictionary, 14th ed., Lewis, Richard J. Sr. ed., copyright 2002 John Wiley & Sons, Inc., available online at http://www.knovel.comiwebiportalibrowseidisplay? EXT KNOVEL DISPLAY bookid=704&VerticalID=0).
A. Breccia et al, "Reaction Between Methanol and Commercial Seed Oils Under Microwave Irradiation" Internation Microwave Power Institute 1999, 34, pp. 3-8.
Zradni, et al, "Minutes Synthesis of Amides from Esters and Amines Under Microwave Irradiation," Fifth International Electronic Conference on Synthetic Organic Chemistry (ECSOC-5), available at http://www.mdpi.org/ecsoc/ecsoc-5/Papers/e0013/e0013.html.
Advanced Organic Chemistry: Reactions, Mechanisms, and Structure; Second Edition, Jerry March, Wiley-Interscience Publication, pp. 324-331 and 382-389, 1977.
Wolf, et al., AOSTRA Journal of Research 3 (1986) "Microwave Assisted Catalytic Conversion of Cyclohesxene" pp. 53-59.
Arfan et al, "Efficient Combination of Recyclable Task Specific Ionic Liquid and Microwave Dielectric Heating for the Synthesis of Lipophilic Esters," Organic Process Research & Development vol. 9, pp. 743-748 (2005).
Arora et al, "A mild and efficient procedure for the conversion of aromatic carboxylic acid esters to secondary amides" Can. J. Chem, vol. 83 (2005), pp. 1137-1140.
Barbosa et al, "Niobium to alcohol mol ratio control of the concuring esterification and etherification reactions promoted by NbCl5 and A1203 catalysts under microwave irradiation," App. Catalysis A: General vol. 338, pp. 9-13 (2008).
Bose et al, "Microwave promoted energy-efficient N-formylation with aqueous formic acid," Tetrahedron Let. vol. 47 (2006), pp. 4605-4607.
C. Mazzocchia et al., "Fatty acid methyl esters synthesis from triglycerides over heterogeneous catalysts in the presence of microwaves" C.R. Chimie 7 (2004) pp. 601-605.
Desai et al, "Thermal and microwave-assisted N-formylation using solid-supported reagents," Tetrahedron Let. vol. 46 (2005), pp. 955-957.
DiLuca et al, "A new, simple procedure for the synthesis of formyl amides," Synlett No. 14 (2004), pp. 2570-257.
Ella Bezdushna et al, Macromolecular Chemistry & Physics, vol. 209, pp. 1942-1947, XP55023715, 2008.
Ella Bezdushna et al: "Microwave-Assisted Esterification of Methacrylic Acid and Polymer-Analogous Esterification of Poly[ethylene-co-(acrylic acid)] with Dissimilar Phenols", Macromolecular Rapid Communications, vol. 208, No. 4, Feb. 19, 2007, pp. 443-448, XP55023715.
English Abstract for CH 681586, Apr. 15, 1993.
English Abstract for CN 1749279, Mar. 2006.
English Abstract for CN 1931980, Mar. 2007.
English Abstract for DE 102005051637, May 3, 2007.
English Abstract for DE 102009001382, Sep. 9, 2010.
English Abstract for DE 2620638, Nov. 24, 1977.
English Abstract for DE 480866, Aug. 1929.
English Abstract for EP 0134995, Mar. 27, 1985.
English Abstract for EP 1256565, Nov. 13, 2002.
English Abstract for JP 10330338, May 1997.
English Abstract for JP 2003321427, Nov. 11, 2003.
English Abstract for JP 2005060256, Mar. 10, 2005.
English Abstract for JP 2005322582, May 2005.
English Abstract for JP 2006181533, Dec. 2004.
English Abstract for JP 2006272055, Mar. 2005.
English Abstract for JP 2008031082, Feb. 14, 2008.
English Abstract for WO 03/090669, Nov. 6, 2003.
English Translation of CN 1351954, Jun. 5, 2002.
English translation of DIN Standard 6162, Mar. 2013.
English translation of JP 2009 263 497, 2009.
Essen et al, "The Velocity of Propagation of Electromagnetic Waves Derived from the Resonant Frequencies of a Cylindrical Cavity Resonator," Proc. R. Soc. Lond. A (1948), vol. 194, pp. 348-361.
Fats and Oils: Formulating and Processing for Applications, Second Ed., O'Brien, CRC Press 2003, Ch. 3, sec. 3.4.2., lines 12-13.
Fatty Acids Division, Soap Association, "Fatty Acids for Chemical Specialties: A symposium of the Soap, Detergents, and Sanitary Chemical Products Division of the Chemical Specialties Manufacturers Association," 1955, pp. 131-147, available online at http://www.aciscience.org/Oleochemical/FattyAcid.aspx.
Gonzalez et al, "Tartradiamide formation by thermolysis of tartaric acid with alkylamines," Tetrahedron Letters vol. 49 (2008 3925-3926.
Ishihara et al, "3,4,5-Trifluorobenzeneboronic Acid as an Extremely Active Amidation Catalyst," J. Org. Chem. vol. 61, (1996), pp. 4196-4197.
Jain et al, "Acetylation of some organic compounds under microwave irradiation," J. Indian Chem. Soc., vol. 84, Feb. 2007, p. 188.
Kangani, et al., "One Pot direct synthesis of amides or oxazolines from carboxylic acids using Deoxo-Fluor reagent," Tetrahedron Letters, vol. 46, (2005), pp. 8917-8920.
Karl G. Kempf et al: "A Procedure for Preparing Aryl Esters of Polyacids. The Conversion of Poly(methacrylic acid) to Poly(phenyl methacrylate)", Macromolecules, vol. 11, No. 5, Sep. 1, 1978, pp. 1038-1041, XP55024162.
Katritzky et al, "Efficient microwave access to polysubstituted amidines from imidoylbenzotriazoles," J. Org. Chem. vol. 71, pp. 3375-3380 (2006).
KIC Chemicals Inc., Capric Acid, available online at http://www.kicgroup.com/capric.htm.
Leadbeater, et al, Continuous-Flow Preparation of Biodiesel Using Microwave Heating:, Energy & Fuels 2007, 21, pp. 1777-1781.

(56) References Cited

OTHER PUBLICATIONS

M. Hajek in A. Loupe "Microwaves in Organic Synthesis", Wiley, 2006, Chapter 13, pp. 615-652.
Machetti, et al., "Parallel Synthesis of an Amide Library Based on the 6,8-Dioxa-3-azabicyclo[3.2.1.]octane Scaffold by direct Aminolysis of Methyl Esters," J. Comb. chem., 2007, vol. 9, pp. 454-461.
Mazzocchia, C., et al., Fast synthesis of biodiesel from trigycerides in presence of microwave, 2006, Advances in Microwave and Radio Frequency Processing, Report of the 8th international conference on microwave and high frequency heatting held in Bayreuth, Germany, Sep. 2001, Springer Berlin Heidelberg, Part V, pp. 370-376 (18 pages).
Mohan et al, "Zeolite catalyzed acylation of alcohols and amines with acetic acid under microwave irradiation," Green Chem. 2006, vol. 8, pp. 368-372.
N. Azcetti et al, "Alkali catalyzed transesterification of cottonseed oil by microwave irradiation" Fuel 86 (2007) pp. 2639-2644, XP022322088.
N. Azcan et al, "Microwave assisted transesterification of rapeseed oil" Fuel 87 (2008) pp. 1781-1788, XP022611169.
N. Leadbeater et al, "Fast, Easy Preparation of Biodiesel Using Microwave Heating" Energy & Fuels 2006, 20, pp. 2281-2283.
N. Saifuddin et al, "Production of Ethyl Ester (Biodiesel) from used Frying Oil: Optimization of Transesterification Process using Microwave Irradiation" Malaysian Journal of Chemistry, 2004, vol. 6, pp. 77-82.
Oliver Kretschmann et al: Microwave-Assisted Synthesis of Associative Hydrogels., Macromolecular Rapid Communications, vol. 28, No. 11, Jun. 1, 2007, pp. 1265-1269, XP55023774.
Petricci et al, "Microwave-assisted acylation of amines, alcohols, and phenols by the use of solid-supported reagents (SSRs)," J. Org. Chem. vol. 69, pp. 7880-7887, (2004).
Pollington, Journal of Organic Chemistry, vol. 56, pp. 1313-1314, 1991.
Reddy et al, "Zirconyl chloride promoted highly efficient solid phase synthesis of amide derivatives," Chinese Chemical Letters, vol. 18 (2007), pp. 1213-1217.
Sebastian Sinnwell et al: "Microwave assisted hydroxyalkylamidation of poly(ethylene-co-acrylic acid) and formation of grafted poly([epsilon]-caprolactone) side chains", Journal of Polymer Science Part A: Polymer Chemistry, vol. 45, No. 16, Aug. 15, 2007, pp. 3659-3667, XP55024233.
Shore, et al, "Catalysis in Capillaries by Pd Thin Films Using Microwave-Assisted continuous-Flow Organic Synthesis (MACOS)" Angewandte Chemie 2006, 118, pp. 2827-2832.
Translation of SIPO Office Action for Application 200980101830.0, May 12, 2012.
Translation of SIPO Search Report for Application 200980101830.0, May 12, 2012.
V. Lertsathapornsuk et al, "Microwave assisted in continous biodiesel production from waste frying palm oil and its performance in a 100 kW diesel generator" Fuel Processing Technology 89 (2008) pp. 1330-1336, XP025681095.
Vacek et al, "Selective enzymic esterification of free fatty acids with n-butanol under microwave irradiation and under classical heating," Biotechnology Letters, vol. 22, pp. 1565-1570 (2000).
Werner et al, "Design and synthesis of a 3,4-dehydroproline amide discovery library," J. Comb. Chem. (2007), 9(4), pp. 677-683.
Zhaoju Yu et al: "Biodegradable polyvinyl alcohol)-graftpoly(epsilon-caprolactone) comb-like polyester: Microwave synthesis and its characterization", Journal of Applied Polymer Science, vol. 104, No. 6, Jun. 15, 2007, pp. 3973-3979, XP55023817.

* cited by examiner

METHOD FOR PRODUCING ALKALINE (METH)ACRYLAMIDES

Ethylenically unsaturated compounds which bear functional groups with basic character are sought after as monomers for preparing functional polymers. Such basic-functionalized copolymers find various uses, for example as a sizing assistant in fiber preparation, in aqueous systems in viscosity modification, in wastewater treatment, as a flocculation assistant in the winning of minerals, and also as an assistant in metal processing and as a detergent additive in lubricant oils. Preferred monomers are especially N-alkylacrylamides and N-alkylmethacrylamides which, as well as the amide group, bear at least one tertiary amino group which imparts basic character, since they have increased hydrolysis stability over corresponding esters. According to the end use, the polymers thus prepared are used as such or after polymer-analogous conversion, for example to quaternary ammonium compounds, N-oxides or else betaines. Often, however, it is difficult to achieve the high molecular weights which are required for the performance properties in such basic-functionalized homo- and copolymers.

In order to cover the growing demand for existing and new applications, various methods for the preparation of ethylenically unsaturated amides bearing tertiary amino groups have been developed. For the preparation of such monomers, the controlled conversion of bifunctional reactants in each case requires particular attention. For instance, the carboxyl group of the parent ethylenically unsaturated carboxylic acid has to be reacted in a controlled manner with the primary or secondary amino group of the unsymmetrically substituted diamine with retention both of the ethylenic double bond and of the tertiary amino group. To date, there has been a reliance on costly and laborious preparation processes in order to achieve a yield of commercial interest. The known preparation processes require highly reactive carboxylic acid derivatives, for example acid anhydrides, acid halides, for example acid chlorides, esters, or in situ activation by the use of coupling reagents, for example N,N'-dicyclohexylcarbodiimide, or very specific and hence expensive catalysts. These preparation processes form in some cases large amounts of undesired by-products such as alcohols, acids and salts, which have to be removed from the product and disposed of. However, the residues of the auxiliaries and by-products which remain in the products can also in some cases bring about very undesired effects. For example, halide ions and also acids lead to corrosion; coupling reagents and the by-products formed by them are in some cases toxic, sensitizing or carcinogenic.

The direct thermal condensation of ethylenically unsaturated carboxylic acid and diamine does not lead to satisfactory results since various side reactions reduce the yield. Examples include a Michael addition of the amine onto the double bond of the ethylenically unsaturated carboxylic acid, uncontrolled thermal polymerization of the ethylenically unsaturated carboxylic acid and/or of the amide formed, oxidation of the amino group during prolonged heating and especially the thermally induced degradation of the amino group. Since such side reactions lead, among other effects, to the formation of additional C=C double bonds, it is possible by this route for amides, once they have formed, to give rise to compounds with two polymerizable centers which, in the later polymerization of the basic (meth)acrylamides, lead to crosslinking and hence insoluble polymers. For example, N-[3-(N,N-dimethylamino)propyl]acrylamide forms, as a result of Hofmann degradation in the presence of acids, N-(allyl)acrylamide, which is a typical crosslinker for polymerization but which is highly undesired for the preparation of soluble polymers and therefore has to be removed.

Iannelli et al., Tetrahedron 2005, 61, 1509-1515 describes the preparation of (R)-1-phenylethylmethacrylamide by condensation of methacrylic acid with (R)-1-phenylethylamine under microwave irradiation.

Goretzki et al., Macromol. Rapid Commun. 2004, 25, 513-516 discloses the microwave-supported synthesis of various (meth)acrylamides directly from (meth)acrylic acid and amine. Various aliphatic and aromatic amines are used.

Gelens et al., Tetrahedron Letters 2005, 46(21), 3751-3754 discloses a multitude of amides which have been synthesized with the aid of microwave radiation.

However, none contains an additional tertiary amino group.

Consequently, a process has been sought for preparing basic amides of ethylenically unsaturated carboxylic acids, in which ethylenically unsaturated carboxylic acids and amines bearing tertiary amino groups can be converted directly and in high yields, i.e. up to quantitative yields, to tertiary amino group-bearing amides or imides or ethylenically unsaturated carboxylic acids. In addition, only minor amounts, if any, of by-products such as Michael adducts and especially polyethylenically unsaturated compounds should occur. Additionally sought have been basic amides of ethylenically unsaturated carboxylic acids which can be used to form particularly high molecular weight homo- and copolymers. In addition, the basic amides prepared in accordance with the invention exhibit virtually no intrinsic color, which is highly advantageous for various applications, for example fiber preparation.

It has been found that amino group-bearing amides or imides of unsaturated $C_3$- to $C_6$-carboxylic acids can be prepared in high yields by directly reacting polyamines bearing at least one primary and/or secondary amino group and additionally at least one tertiary amino group with $C_3$- to $C_6$-carboxylic acids by irradiating with microwaves. Surprisingly, in spite of the presence of acids, no significant Hofmann elimination of the tertiary amino group occurs.

The invention provides a process for preparing basic amides or imides of ethylenically unsaturated $C_3$- to $C_6$-carboxylic acids by reacting amines which contain at least one primary and/or secondary amino group and at least one tertiary amino group with ethylenically unsaturated $C_3$- to $C_6$-carboxylic acids to give an ammonium salt, and then converting this ammonium salt to the basic amide or imide under microwave irradiation, with the proviso that the primary and/or secondary amino group does not comprise any alkoxy groups.

The invention further provides basic amides or imides of ethylenically unsaturated $C_3$- to $C_6$-carboxylic acids, which are essentially free of halide ions and by-products originating from coupling reagents and are preparable by reacting amines which bear at least one primary and/or secondary amino group and at least one tertiary amino group with ethylenically unsaturated $C_3$- to $C_6$-carboxylic acids to give an ammonium salt, and then converting this ammonium salt to the basic amide or imide under microwave irradiation, with the proviso that the primary and/or secondary amino group does not comprise any alkoxy groups.

Basic amides and imides are understood to mean amides and imides whose amide or imide nitrogen atom bears at least one hydrocarbon radical substituted by at least one tertiary amino group. Tertiary amino groups in the context of the present invention are structural units in which one nitrogen atom does not bear an acidic proton. For instance, the nitrogen of the tertiary amino group may bear three hydrocarbon radicals or else be part of a heteroaromatic system. Fatty acid amides free of halide ions do not contain any amounts of these ions over and above the ubiquitous amounts of halide ions.

The proviso that the primary and/or secondary amino group does not comprise any alkoxy groups means that the primary and/or secondary amino group does not bear or, if a plurality of such groups are present, none of them bear, a substituent which comprises alkoxy groups.

Ethylenically unsaturated $C_3$- to $C_6$-carboxylic acids are understood to mean those carboxylic acids which have from 3 to 6 carbon atoms and possess a C=C double bond conjugated to a carboxyl group. Preferred ethylenically unsaturated carboxylic acids may bear one or more carboxyl groups, especially one or two carboxyl groups. Examples of carboxylic acids suitable in accordance with the invention are acrylic acid, methacrylic acid, crotonic acid, 2,2-dimethylacrylic acid, maleic acid, fumaric acid and itaconic acid. Particular preference is given to acrylic acid and methacrylic acid.

Also in the case of use of ethylenically unsaturated dicarboxylic acids in the form of their anhydrides, for example maleic anhydride, the process according to the invention is advantageous. The condensation of the amidocarboxylic acid which is formed as an intermediate from dicarboxylic acid and amine bearing primary and/or secondary and tertiary amino groups leads, in contrast to the thermal condensation, in a high yield, to tertiary amino group-bearing imides of ethylenically unsaturated carboxylic acids.

Amines suitable in accordance with the invention possess two or more amino groups. At least one of these amino groups is tertiary, which means that it bears three alkyl radicals or is part of a heteroaromatic system. At least one amino group bears one or two hydrogen atoms, preferably two hydrogen atoms.

In a preferred embodiment, the invention provides a process for preparing basic amides or imides of ethylenically unsaturated $C_3$- to $C_6$-carboxylic acids, in which amines of the formula

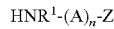

in which
$R^1$ is hydrogen, $C_1$-$C_{12}$-alkyl, $C_5$-$C_{12}$-cycloalkyl, $C_6$-$C_{12}$-aryl, $C_7$-$C_{12}$-aralkyl or a heteroaromatic group having from 5 to 12 ring members,
A is an alkylene radical having from 1 to 12 carbon atoms, a cycloalkylene radical having from 5 to 12 ring members, an arylene radical having from 6 to 12 ring members or a heteroarylene radical having from 5 to 12 ring members,
n is 0 or 1,
Z is a group of the formula —$NR^2R^3$ or a nitrogen-containing cyclic hydrocarbon radical having at least 5 ring members and
$R^2$ and $R^3$ are each independently $C_1$- to $C_{20}$-hydrocarbon radicals or polyoxyalkylene radicals,
and also the basic amides or imides of ethylenically unsaturated $C_3$- to $C_6$-carboxylic acids, which are preparable by this process and which are essentially free of halide ions and by-products originating from coupling reagents.

Preferably, $R^1$ is hydrogen or methyl, especially hydrogen.

Preferably, A is a linear or branched alkylene radical having from 1 to 12 carbon atoms and n is 1.

More preferably, A, when Z is a group of the formula —$NR^2R^3$, is a linear or branched alkylene radical having 2, 3 or 4 carbon atoms, especially an ethylene radical or a linear propylene radical. When Z, in contrast, is a nitrogen-containing cyclic hydrocarbon radical, particular preference is given to compounds in which A is a linear alkylene radical having 1, 2 or 3 carbon atoms, especially a methylene, ethylene or a linear propylene radical.

Cyclic radicals preferred for the structural element A may be mono- or polycyclic and, for example, contain two or three ring systems. Preferred ring systems possess 5, 6 or 7 ring members. They preferably contain a total of from about 5 to 20 carbon atoms, especially from 6 to 10 carbon atoms. Preferred ring systems are aromatic and contain only carbon atoms. In a specific embodiment, the structural elements A are also formed from arylene radicals. The structural element A may bear substituents, for example alkyl radicals, halogen atoms, halogenated alkyl radicals, nitro, cyano, nitrile, hydroxyl and/or hydroxyalkyl groups. When A is a monocyclic aromatic hydrocarbon, the amino groups or substituents bearing amino groups are preferably present also ortho or para to one another.

Z is preferably a group of the formula —$NR^2R^3$. In this group, $R^2$ and $R^3$ are preferably each independently aliphatic, aromatic and/or araliphatic hydrocarbon radicals having from 1 to 20 carbon atoms. Particularly preferred $R^2$ and $R^3$ are alkyl radicals. When $R^2$ and/or $R^3$ are alkyl radicals, they preferably bear from 1 to 14 carbon atoms, for example from 1 to 6 carbon atoms. These alkyl radicals may be linear, branched and/or cyclic. $R^2$ and $R^3$ are more preferably alkyl radicals having from 1 to 4 carbon atoms, for example methyl, ethyl, n-propyl, isopropyl, n-butyl and isobutyl.

The $R^2$ and $R^3$ radicals may be substituted by heteroatoms, for example O and/or S, and/or bear substituents comprising such heteroatoms. However, they preferably do not contain more than 1 heteroatom per 2 carbon atoms. Thus, in a further preferred embodiment, $R^2$ and/or $R^3$ are each independently polyoxyalkylene radicals of the formula

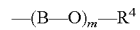

in which
B is a linear or branched $C_2$-$C_4$-alkylene radical, especially a group of the formula —$CH_2$—$CH_2$— and/or —CH($CH_3$)—$CH_2$—,
m is from 1 to 100, preferably from 1 to 20, and
$R^4$ is hydrogen, an alkyl radical having from 1 to 20 carbon atoms, a cycloalkyl radical having from 5 to 12 ring atoms, an aryl radical having from 6 to 12 ring atoms, an aralkyl radical having from 7 to 30 ring atoms, a heteroaryl radical having from 5 to 12 ring atoms or a heteroaralkyl radical having from 6 to 12 carbon atoms.

Aromatic radicals particularly suitable as $R^2$ and/or $R^3$ include ring systems having at least 5 ring members. They may contain heteroatoms such as S, O and N. Araliphatic radicals particularly suitable as $R^2$ and/or $R^3$ include ring systems which have at least 5 ring members and are bonded to the nitrogen via a $C_1$-$C_6$-alkyl radical. They may contain heteroatoms such as S, O and N. The aromatic and also the araliphatic radicals may bear further substituents, for example alkyl radicals, halogen atoms, halogenated alkyl radicals, nitro, cyano, nitrile, hydroxyl and/or hydroxyalkyl groups.

In a further preferred embodiment, Z is a nitrogen-containing cyclic hydrocarbon radical whose nitrogen atom is incapable of forming amides. The cyclic system may be mono-, di- or else polycyclic. It preferably contains one or more five- and/or six-membered rings. This cyclic hydrocarbon may contain one or more, for example two or three, nitrogen atoms which do not bear any acidic protons; it more preferably contains one nitrogen atom. Particularly suitable are nitrogen-containing aromatics whose nitrogen is involved in the formation of an aromatic π-electron sextet, for example pyridine. Equally suitable are nitrogen-containing heteroaliphatics whose nitrogen atoms do not bear any protons and, for example, are all saturated by alkyl radicals. The bond of Z to A or the group of the formula NHR$^1$ (if n=0) is effected here preferably through a nitrogen atom of the heterocycle, for example in the case of 1-(3-aminopropyl)pyrrolidine. The cyclic hydrocarbon represented by Z may bear further substituents, for example $C_1$-$C_{20}$-alkyl radicals, halogen atoms, halogenated alkyl radicals, nitro, cyano, nitrile, hydroxyl and/or hydroxyalkyl groups.

Examples of suitable amines are N,N-dimethylethylenediamine, N,N-dimethyl-1,3-propanediamine, N,N-diethyl-1,3-propanediamine, N,N-dimethyl-2-methyl-1,3-propanediamine, N,N-(2'-hydroxyethyl)-1,3-propanediamine, 1-(3-aminopropyl)-pyrrolidine, 1-(3-aminopropyl)-4-methylpiperazine, 3-(4-morpholino)-1-propylamine, 2-aminothiazole, the various isomers of N,N-dimethylaminoaniline, of aminopyridine, of aminomethylpyridine, of aminomethylpiperidine and of aminoquinoline, and also 2-aminopyrimidine, 3-aminopyrazole, aminopyrazine and 3-amino-1,2,4-triazole.

The process is especially suitable for preparing N-[3-(N,N-dimethyl-amino)propyl]acrylamide, N-[3-(N,N-dimethylamino)propyl]methacrylamide, N-[3-(N,N-dimethylamino)propyl]crotonylamide, N-[3-(N,N-dimethyl-amino)propyl]itaconylimide, N-[(pyridin-4-yl)methyl]acrylamide and N-[(pyridin-4-yl)methyl]methacrylamide.

In the process according to the invention, it is possible to react ethylenically unsaturated carboxylic acid and amine with one another in any desired ratios. For the preparation of the pure monomers, suitable molar ratios between ethylenically unsaturated carboxylic acid and amine are preferably from 10:1 to 1:10, preferably from 2:1 to 1:2, especially from 1.0:1.2 to 1.2:1.0 and in particular equimolar.

In many cases, it has been found to be advantageous to work with a small excess of amine, i.e. molar ratios of amine to carboxylic acid of at least 1.01:1.00 and especially between 1.02:1.00 and 1.2:1.0, for example between 1.05:1.0 and 1.1:1. This converts the acid virtually quantitatively to the basic amide. This process is particularly advantageous when the amine bearing at least one primary and/or secondary and at least one tertiary amino group used is volatile. "Volatile" means here that the amine has a boiling point at standard pressure of preferably below 200° C., for example below 150° C., and can thus be removed from the amide by distillation.

When the inventive basic amides or imides are to be used to prepare copolymers with the ethylenically unsaturated $C_3$-$C_6$-carboxylic acids used to prepare them, it is also possible to use higher excesses of ethylenically unsaturated carboxylic acid. For instance, it has been found to be useful to work with molar ratios of carboxylic acid to amine of at least 1.01:1.00 and especially between 1.02:1.00 and 50:1.0, for example between 1.05:1.0 and 10:1. The acid excess can then be used for in-situ preparation of copolymers with the inventive monomers.

The amides/imides are prepared by converting the ethylenically unsaturated carboxylic acid and the amine to the ammonium salt and then irradiating the salt with microwaves. The ammonium salt is preferably generated in situ and not isolated. The temperature rise caused by the microwave irradiation is preferably limited to a maximum of 300° C. by regulating the microwave intensity and/or cooling the reaction vessel. It has been found to be particularly useful to perform the conversion at temperatures between 100 and 240° C. and especially between 120 and 200° C., for example at temperatures between 125 und 175° C.

The duration of the microwave irradiation depends on various factors, such as the reaction volume, the geometry of the reaction chamber and the desired conversion. Typically, the microwave irradiation is undertaken over a period of less than 60 minutes, preferably between 0.01 second and 15 minutes, more preferably between 0.1 second and 10 minutes and especially between 1 second and 5 minutes, for example between 5 seconds and 2 minutes. The intensity (power) of the microwave radiation is adjusted such that the reaction mixture reaches the desired reaction temperature within a minimum time. To subsequently maintain the temperature, the reaction mixture can be irradiated further with reduced and/or pulsed power. To maintain the maximum temperature with simultaneously maximum microwave incidence, it has been found to be useful to cool the reaction mixture, for example, by means of a cooling jacket, cooling tubes present in the reaction chamber through intermittent cooling between different irradiation zones, and/or by evaporative cooling by means of external heat exchangers. In a preferred embodiment, the reaction product is cooled directly after the microwave irradiation has ended as rapidly as possible to temperatures below 120° C., preferably below 100° C. and especially below 60° C.

Preference is given to performing the reaction at pressures between 0.1 and 200 bar and especially between 1 bar (atmospheric pressure) and 50 bar. It has been found to be particularly useful to work in closed vessels in which operation is effected above the boiling point of the reactants and/or products, of the solvent which may be present and/or above the water of reaction formed during the reaction. Typically, the pressure which is established owing to the heating of the reaction mixture is sufficient for successful performance of the process according to the invention. However, it is also possible to work under elevated pressure and/or with application of a pressure profile. In a further preferred variant of the process according to the invention, atmospheric pressure, as established, for example, in the open vessel, is employed.

To prevent side reactions and to prepare very pure products, it has been found to be useful to perform the process according to the invention in the presence of an inert protective gas, for example nitrogen, argon or helium.

In a preferred embodiment, the reaction is accelerated or completed by working in the presence of dehydrating catalysts. Preference is given to working in the presence of an acidic inorganic, organometallic or organic catalyst, or mixtures of a plurality of these catalysts.

Examples of acidic inorganic catalysts in the context of the invention include sulfuric acid, phosphoric acid, phosphonic acid, hypophosphorous acid, aluminum sulfate hydrate, alum, acidic silica and acidic aluminum hydroxide. It is additionally possible to use, for example, aluminum compounds of the formula Al(OR$^5$)$_3$ and titanates of the formula Ti(OR$^5$)$_4$ as acidic inorganic catalysts, where the R$^5$ radicals may each be the same or different and are each independently selected from $C_1$-$C_{10}$-alkyl radicals, for example methyl, ethyl, n-propyl, isopropyl, n-butyl, isobutyl, sec-butyl, tert-butyl, n-pentyl, isopentyl, sec-pentyl, neo-pentyl, 1,2-dimethylpropyl, isoamyl, n-hexyl, sec-hexyl, n-heptyl, n-octyl, 2-ethylhexyl, n-nonyl or n-decyl, $C_3$-$C_{12}$-cycloalkyl radicals, for example cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl. The R$^5$ radicals in Al(OR$^5$)$_3$ or Ti(OR$^5$)$_4$ are preferably each the same and are selected from isopropyl, butyl and 2-ethylhexyl.

Preferred acidic organometallic catalysts are, for example, selected from dialkyltin oxides (R$^5$)$_2$SnO where R$^5$ is as defined above. A particularly preferred representative of acidic organometallic catalysts is di-n-butyltin oxide, which is commercially available as so-called oxo-tin or as Fascat® brands.

Preferred acidic organic catalysts are acidic organic compounds with, for example, phosphate groups, sulfonic acid groups, sulfate groups or phosphonic acid groups. Particularly preferred sulfonic acids contain at least one sulfonic acid group and at least one saturated or unsaturated, linear, branched and/or cyclic hydrocarbon radical having from 1 to 40 carbon atoms and preferably having from 3 to 24 carbon atoms. Especially preferred are aromatic sulfonic acids, especially alkylaromatic monosulfonic acids having one or more $C_1$-$C_{28}$-alkyl radicals and especially those having $C_3$-$C_{22}$-alkyl radicals. Suitable examples are methanesulfonic acid, butanesulfonic acid, benzenesulfonic acid, p-toluenesulfonic acid, xylenesulfonic acid, 2-mesitylenesulfonic acid, 4-ethylbenzenesulfonic acid, isopropylbenzenesulfonic acid, 4-butylbenzenesulfonic acid, 4-octylbenzenesulfonic acid, dodecylbenzenesulfonic acid, didodecylbenzenesulfonic acid, naphthalenesulfonic acid. It is also possible to use acidic ion exchangers as acidic organic catalysts, for example sulfonic acid group-containing poly(styrene) resins which have been crosslinked with about 2 mol % of divinylbenzene.

Particularly preferred for the performance of the process according to the invention are boric acid, phosphoric acid, polyphosphoric acid and polystyrenesulfonic acid. Especially preferred are titanates of the formula $Ti(OR^5)_4$ and especially titanium tetrabutoxide and titanium tetraisopropoxide.

If it is desired to use acidic inorganic, organometallic or organic catalysts, from 0.01 to 10% by weight, preferably from 0.02 to 2% by weight, of catalyst is used in accordance with the invention. A particularly preferred embodiment works without catalyst.

In a further preferred embodiment, the microwave irradiation is performed in the presence of acidic solid catalysts. The solid catalyst is suspended in the ammonium salt which has optionally been admixed with solvent, or, in continuous processes, the ammonium salt optionally admixed with solvent is advantageously passed over a fixed bed catalyst and exposed to microwave radiation. Suitable solid catalysts are, for example, zeolites, silica gel, montmorillonite and (partly) crosslinked polystyrenesulfonic acid, which may optionally be impregnated with catalytically active metal salts. Suitable acidic ion exchangers which are based on polystyrenesulfonic acids and can be used as solid-phase catalysts are obtainable, for example, from Rohm&Haas under the name Amberlyst®.

It has been found to be useful to work in the presence of solvents in order, for example, to lower the viscosity of the reaction medium, to fluidize the reaction mixture if it is heterogeneous, and/or to improve the heat removal, for example by means of evaporative cooling. For this purpose, it is possible in principle to use all solvents which are inert under the reaction conditions employed and do not react with the reactants or the products formed. An important factor in the selection of suitable solvents is their polarity, which determines firstly the solution properties and secondly the degree of interaction with microwave radiation. A particularly important factor in the selection of suitable solvents is their dielectric loss $\in''$. The dielectric loss $\in''$ describes the proportion of microwave radiation which is converted to heat when a substance interacts with microwave radiation. The latter value has been found to be a particularly important criterion for the suitability of a solvent for the performance of the process according to the invention. It has been found to be particularly useful to work in solvents which exhibit minimum microwave absorption and thus make only a small contribution to the heating of the reaction system. Solvents preferred for the process according to the invention possess a dielectric loss $\in''$, measured at room temperature and 2450 MHz, of less than 10 and preferably less than 1, for example less than 0.5. An overview of the dielectric loss of different solvents can be found, for example, in "Microwave Synthesis" by B. L. Hayes, CEM Publishing 2002. Suitable solvents for the process according to the invention are especially solvents with $\in''$ values below 10, such as N-methylpyrrolidone, N,N-dimethylformamide or acetone, and especially solvents with $\in''$ values below 1. Examples of particularly preferred solvents with $\in''$ values below 1 are aromatic and/or aliphatic hydrocarbons, for example toluene, xylene, ethylbenzene, tetralin, hexane, cyclohexane, decane, pentadecane, decalin, and commercial hydrocarbon mixtures such as petroleum fractions, kerosene, Solvent Naphtha, ®Shellsol AB, ®Solvesso 150, ®Solvesso 200, ®Exxsol, ®Isopar and ®Shellsol types. Solvent mixtures which have $\in''$ values preferably below 10 and especially below 1 are equally preferred for the performance of the process according to the invention. In principle, the process according to the invention is also possible in solvents with $\in''$ values of 10 and higher, but this requires particular measures for complying with the maximum temperature and often leads to reduced yields. When working in the presence of solvents, the proportion thereof in the reaction mixture is preferably between 2 and 95% by weight, especially between 5 and 90% by weight and in particular between 10 and 75% by weight, for example between 30 and 60% by weight. Particular preference is given to performing the reaction without solvent.

To prevent uncontrolled thermal polymerization during the condensation, it has been found to be useful to perform it in the presence of polymerization inhibitors. Particularly suitable polymerization inhibitors are those based on phenols such as hydroquinone, hydroquinone monomethyl ether, and on sterically hindered phenols such as 2,6-di-tert-butylphenol or 2,6-di-tert-butyl-4-methylphenol. Equally suitable are thiazines such as phenothiazine or methylene blue, and nitroxides, especially sterically hindered nitroxides, i.e. nitroxides of secondary amines which each bear three alkyl groups on the carbon atoms which are adjacent to the nitroxide group, where two of these alkyl groups, especially those which are not present on the same carbon atom, with the nitrogen atom of the nitroxide group or the carbon atom to which they are bonded, form a saturated 5- or 6-membered ring, for example in 2,2,6,6-tetramethylpiperidine 1-oxyl (TEMPO) or 4-hydroxy-2,2,6,6-tetramethylpiperidine 1-oxyl (OH-TEMPO). Equally suitable are mixtures of the aforementioned inhibitors, mixtures of the aforementioned inhibitors with oxygen, for example in the form of air, and mixtures of mixtures of the aforementioned inhibitors with air. These are added to the reaction mixture or to one of the reactants preferably in amounts of from 1 to 1000 ppm and especially in amounts of from 10 to 200 ppm based on the ethylenically unsaturated carboxylic acid.

The microwave irradiation is typically performed in units which possess a reaction chamber composed of a material very substantially transparent to microwaves, into which microwave radiation generated in a microwave generator is injected through suitable antenna systems. Microwave generators, for example the magnetron and the klystron, are known to those skilled in the art.

Microwaves refer to electromagnetic rays having a wavelength between about 1 cm and 1 m and frequencies between about 300 MHz and 30 GHz. This frequency range is suitable in principle for the process according to the invention. Preference is given to using, for the process according to the invention, microwave radiation with the frequencies approved for industrial, scientific and medical applications of 915 MHz, 2.45 GHz, 5.8 GHz or 27.12 GHz. It is possible to work either in monomode or quasi-monomode, or else in multimode. In the case of monomode, which places high demands on the geometry and size of the apparatus and reaction chamber, a very high energy density is generated by a standing wave, especially at the maximum thereof. In multimode, in contrast, the entire reaction chamber is irradiated substantially homogeneously, which enables, for example, greater reaction volumes.

The microwave power to be injected into the reaction vessel for the performance of the process according to the invention is dependent especially on the geometry of the reaction chamber and hence of the reaction volume, and on the duration of the irradiation required. It is typically between 100 W and several hundred kW, and especially between 200 W and 100 kW, for example between 500 W and 70 kW. It can be applied at one or more sites in the reactor. It can be generated by means of one or more microwave generators.

The reaction can be carried out batchwise or preferably continuously in a flow tube, for example. It can additionally be performed in semibatchwise processes, for example continuous stirred reactors or cascade reactors. In a preferred embodiment, the reaction is performed in a closed vessel, in which case the condensate which forms and if appropriate reactants and, where present, solvents lead to a pressure buildup. After the reaction has ended, the elevated pressure can be used by decompression to volatilize and remove water of reaction, and if appropriate solvents and excess reactants, and/or cool the reaction product. In a further embodiment, the water of reaction formed, after cooling and/or decompression, is removed by customary processes, for example phase separation, distillation and/or absorption. The process according to the invention can be effected equally successfully in an open vessel with evaporative cooling and/or separation of the water of reaction.

In a preferred embodiment, the process according to the invention is performed in a batchwise microwave reactor. The microwave irradiation is undertaken in a stirred vessel. To remove excess heat, cooling elements are preferably present in the reaction vessel, for example cooling fingers or cooling coils, or reflux condensers flanged onto the reaction vessel for evaporative cooling of the reaction medium. For the irradiation of relatively large reaction volumes, the microwave here is preferably operated in multimode. The batchwise embodiment of the process according to the invention allows, through variation of the microwave power, rapid or else slow heating rates, and especially the maintenance of the temperature over prolonged periods, for example several hours. The reactants and any solvents and further assistants can be initially charged in the reaction vessel before commencement of the microwave irradiation. They preferably have temperatures below 100° C., for example between 10° C. and 35° C. In a preferred embodiment, the reactants or portions thereof are not added to the reaction vessel until during the irradiation with microwaves. In a further preferred embodiment, the batchwise microwave reactor is operated with continuous supply of reactants and continuous discharge of reaction mixture in the form of a semibatchwise or cascade reactor.

In a particularly preferred embodiment, the process according to the invention is performed in a continuous microwave reactor. To this end, the reaction mixture is conducted through a pressure-resistant reaction tube which is inert toward the reactants, is very substantially transparent to microwaves and is built into a microwave oven. This reaction tube preferably has a diameter of from one millimeter to approx. 50 cm, especially between 2 mm and 35 cm, for example between 5 mm and 15 cm. Reaction tubes are understood here to mean vessels whose ratio of length diameter is greater than 5, preferably between 10 and 100 000, more preferably between 20 and 10 000, for example between 30 and 1000. In a specific embodiment, the reaction tube is configured in the form of a jacketed tube through whose interior and exterior the reaction mixture can be conducted successively in countercurrent, in order, for example, to increase the thermal conduction and energy efficiency of the process. The length of the reaction tube is understood to mean the total distance through which the reaction mixture flows. Over its length, the reaction tube is surrounded by at least one microwave radiator, but preferably by more than one, for example two, three, four, five, six, seven, eight or more microwave radiators. The microwaves are preferably injected through the tube jacket. In a further preferred embodiment, the microwaves are injected by means of at least one antenna via the tube ends. The reaction tube is typically provided at the inlet with a metering pump and a manometer, and at the outlet with a pressure-retaining valve and a heat exchanger. The polyamine and $C_3$-$C_6$-carboxylic acid reactants, each independently optionally diluted with solvent, are preferably not mixed until shortly before entry into the reaction tube. Additionally preferably, the reactants are supplied to the process according to the invention in liquid form at temperatures below 100° C., preferably between 10 and 80° C., for example between 20 and 50° C.

Variation of tube cross section, length of the irradiation zone (this is understood to mean the proportion of the reaction tube in which the reaction mixture is exposed to microwave irradiation), flow rate, geometry of the microwave radiators, the microwave power injected and the temperature attained as a result are used to adjust the reaction conditions such that the maximum reaction temperature is attained as rapidly as possible and the residence time at maximum temperature remains sufficiently short that as low as possible a level of side reactions or further reactions occurs. Preference is given to operating the continuous microwave reactor in monomode or quasi-monomode. The residence time in the reaction tube is generally below 30 minutes, preferably between 0.01 second and 15 minutes, for example between 0.1 second and 5 minutes, for example between 1 second and 3 minutes. To complete the reaction, if appropriate after intermediate cooling, the reaction mixture can pass through the reactor more than once, in which case product and/or by-product formed can optionally be removed in an intermediate step. It has been found to be particularly useful when the reaction product, immediately after leaving the reaction tube, is cooled, for example by jacket cooling or decompression.

It was particularly surprising that, in spite of the only very short residence time of the ammonium salt in the microwave field in the flow tube with continuous flow, such a substantial amidation takes place without formation of significant amounts of by-products. In the case of a corresponding reaction of these ammonium salts in a flow tube with thermal jacket heating, extremely high wall temperatures are required to achieve suitable reaction temperatures, and lead to polymerization and formation of Mannich adduct and various amine derivatives, but only to the formation of minor amounts of basic amides of ethylenically unsaturated carboxylic acids.

To complete the reaction, it has been found to be useful in many cases to expose the resulting crude product, after removing water of reaction and optionally discharging product and/or by-product, again to microwave irradiation.

Typically, amides prepared by the inventive route are obtained in a purity sufficient for further use. For specific requirements, they can, however, be purified further by customary purification processes such as distillation, recrystallization, filtration and chromatographic processes.

The amides prepared in accordance with the invention are suitable especially for homopolymerization or else for copolymerization with further ethylenically unsaturated compounds. Based on the total mass of the (co)polymers, their contents of amides prepared in accordance with the invention may be from 0.1 to 100% by weight, preferably from 20 to 99.5% by weight, more preferably from 50 to 98% by weight. The comonomers used may be all ethylenically unsaturated compounds whose reaction parameters allow copolymerization with the amides prepared in accordance with the invention in the particular reaction media.

Preferred comonomers are ethylenically unsaturated carboxylic acids, for example (meth)acrylic acid, maleic acid, fumaric acid and itaconic acid, and the anhydrides, esters, amides and salts thereof. Also suitable as comonomers are sulfonic acids, for example styrenesulfonic acid, vinylsulfonic acid, allylsulfonic acid and methallylsulfonic acid, and phosphoric acids, for example vinylphosphonic acid and allylsulfonic acid, and salts thereof.

Preferred esters of these acids are those with aliphatic alcohols having from 1 to 30 carbon atoms, cycloaliphatic alcohols having from 5 to 30 carbon atoms, and arylaliphatic or aromatic alcohols having from 6 to 30 carbon atoms, for example methyl acrylate, methyl methacrylate, lauryl methacrylate and stearyl acrylate. The aliphatic radicals may be linear or branched and saturated or unsaturated.

Preferred amides of these acids derive from ammonia and amines having one or two hydrocarbon radicals having in each case from 1 to 24 carbon atoms. Examples of particularly preferred amides are acrylamide, methacrylamide, N,N-dimethylacrylamide, N,N-diethylacrylamide and N,N-diisopropylacrylamide.

Preferred salts of these acids bear, for example, $Li^+$, $Na^+$, $K^+$, $Mg^{2+}$, $Ca^{2+}$, $Al^{3+}$, $NH_4^+$, monoalkylammonium, dialkylammonium, trialkylammonium and/or tetraalkylammonium cations, where the alkyl substituents of the ammonium ions may each independently be hydrocarbon radicals having from 1 to 22 carbon atoms, hydroxyalkyl groups having from 3 to 10 carbon atoms, or poly(oxyalkylene) groups. The degree of neutralization of the carboxylic acids may be between 0 and 100%.

Likewise preferred as comonomers are vinyl esters of carboxylic acids having from 2 to 20 carbon atoms, for example vinyl acetate, vinyl propionate, vinyl 2-ethylhexanoate and vinyl neodecanoate, open-chain N-vinylamides, for example N-vinylformamide (VIFA), N-vinylmethylformamide, N-vinyl methylacetamide (VIMA) and N-vinylacetamide, cyclic N-vinylamides (N-vinyllactams) with a ring size of from 3 to 9, for example N-vinylpyrrolidone (NVP) and N-vinylcaprolactam, alkoxylated acrylic and methacrylic acids and acrylamides and methacrylamides, for example hydroxyethyl methacrylate, hydroxymethylmethacrylamide, hydroxyethylmethacrylamide, hydroxypropylmethacrylamide and mono-[2-(methacryloyloxy)ethyl]succinate, N,N-dimethylamino methacrylate and diethylaminomethyl methacrylate. Examples of further preferred comonomers are acrylonitrile, acryl- and methacrylamidoglycolic acid, vinyl ethers of alcohols having from 1 to 22 carbon atoms, olefins having from 2 to 20 carbon atoms, styrene, alkylstyrenes, vinyl chloride, vinylidene chloride, tetrafluoroethylene, 2- and 4-vinylpyridine, and glycidyl methacrylate. Mixtures of different comonomers are equally suitable for copolymerization.

The process according to the invention allows very rapid and inexpensive preparation of basic amides of unsaturated carboxylic acids in high yields and with high purity. No significant amounts of by-products are obtained. The products prepared by the process according to the invention are additionally nearly colorless, i.e. they possess APHA color numbers of below 100 and often below 50, for example between 30 and 15. Therefore, typically no workup or reprocessing steps are required. Such rapid and selective reactions cannot be achieved by conventional methods and were also not to be expected solely through heating to high temperatures. Since the amides prepared by the process according to the invention and the (co)polymers derived therefrom, by virtue of the process, contain no residues of coupling reagents or conversion products thereof, they can also be used without any problem in toxicologically sensitive fields, for example cosmetic and pharmaceutical formulations. In addition, owing to their freedom from halide ions as a result of the process, they can be used in corrosion-endangered areas, for example in plants for mineral oil and natural gas extraction and processing.

EXAMPLES

The reactions under microwave irradiation were effected in a "Discover" single-mode microwave reactor from CEM at a frequency of 2.45 GHz. The reaction vessels were cooled by means of compressed air. Owing to pressure conditions in the reaction vessels, the temperature had to be measured via an IR sensor at the base of the cuvette. Comparative tests with a glass fiber optic system immersed into the reaction mixture found that the temperature in the reaction medium, within the temperature range relevant here, is from about 50 to 80° C. above the temperature measured at the cuvette base with the IR sensor.

The batchwise reactions were effected in closed, pressure-resistant glass cuvettes with a capacity of 8 ml with magnetic stirring. Continuous reactions were effected in pressure-resistant cylindrical glass cuvettes (approx. 10×1.5 cm; reaction volume approx. 15 ml) with an inlet tube ending above the cuvette base, and product outlet at the upper end of the cuvette (jacketed tube). The pressure which builds up during the reaction was limited to a maximum of 20 bar by means of a pressure-retaining valve and decompressed into a reservoir. The ammonium salt was pumped into the cuvette through the inlet tube and the residence time in the irradiation zone was adjusted to about 1 minute by modifying the pump output. The ethylenically unsaturated carboxylic acids used were each stabilized with 200 ppm of hydroquinone monomethyl ether.

The products were analyzed by means of $^1$H NMR spectroscopy at 500 MHz in $CDCl_3$ or by means of GC-MS. Water determinations were effected by means of Karl-Fischer titration.

Example 1

Preparation of
N-(3-(N,N-dimethylamino)propyl)methacrylamide 1 g of N,N-dimethylaminopropylamine was cooled while an equimolar amount of methacrylic acid was added and mixed in. After the exothermicity had abated, the ammonium salt thus obtained was exposed to microwave irradiation of 100 W in a closed cuvette with maximum cooling power for 1 minute. A temperature of 150° C. measured by means of an IR sensor was attained, and the pressure rose to 10 bar. Subsequently, the reaction mixture was cooled to 30° C. within 2 minutes.

The resulting reaction product contained, as main components, 82% N-(3-(N,N-dimethylamino)propyl)methacrylamide, 4% Michael adduct, 9% water and unconverted reactants. After the reaction mixture had been dried over $MgSO_4$, repeated irradiation with 100 W microwaves for 1 minute and drying over molecular sieve, N-(3-(N,N-dimethylamino)propyl)methacrylamide was obtained with more than 98% purity. The APHA color number was 45.

Example 2

Preparation of
N-(3-(N,N-dimethylamino)propyl)acrylamide 2 g of N,N-dimethylaminopropylamine were cooled while an equimolar amount of acrylic acid was added and mixed in. After the exothermicity had abated, the ammonium salt thus obtained was exposed to microwave irradiation of 25 W in a closed cuvette with maximum cooling power for 1 minute. A temperature of 80° C. measured by means of an IR sensor was attained at a pressure of about 1.3 bar. After the end of irradiation, the reaction mixture was cooled to 30° C. within 2 minutes.

The resulting reaction product contained, as main components, 61% N-(3-(N,N-dimethylamino)propyl)acrylamide, 12% Michael adduct, 7% water and unconverted reactants. After the reaction mixture had been dried over $MgSO_4$, repeated irradiation with 50 W microwaves for 1 minute and drying over molecular sieve, N-(3-(N,N-dimethylamino)propyl)acrylamide was obtained with more than 95% purity. The APHA color number was 35.

Example 3

Preparation of
N-(p-[N,N-dimethylamino]phenylene)methacrylamide 1 g of p-(N,N-dimethyl)phenylenediamine was cooled while two molar equivalents of methacrylic acid were added and mixed in. After the exothermicity had abated, the ammonium salt thus obtained was exposed to a microwave power of 150 W in a closed cuvette with maximum cooling power. The mixture was heated to 185° C. within one minute and this temperature was maintained over 10 minutes with air cooling of the cuvette, in the course of which the pressure rose gradually to 2 bar. Subsequently, the mixture was cooled to below 50° C. by air cooling within two minutes.

In the crude product, 92% of the p-(N,N-dimethyl)phenylenediamine had been converted to N-(p-[N,N-dimethylamino]phenylene)methacrylamide. The further constituents of the crude product were water of reaction and unconverted reactants. After removal of the water of reaction, repeated microwave irradiation over 10 minutes and distillative removal of excess methacrylic acid and water of reaction, 98% N-(p-[N,N-dimethylamino]phenylene)methacrylamide was obtained. The APHA color number was 41.

Example 4

Preparation of N-(Triazolyl)Methacrylamide 0.5 g of 3-amino-1,2,4-triazole was cooled while the equimolar amount of methacrylic acid was added and mixed in. After the exothermicity had abated, the ammonium salt thus obtained was irradiated with a microwave power of 100 W in a closed cuvette and heated to 150° C. within one minute, and this temperature was maintained with air cooling of the cuvette over 2 minutes, in the course of which the pressure rose to 2 bar. Subsequently, the mixture was cooled to 50° C. by air cooling within two minutes.

The crude product contained 86% N-(triazolyl)methacrylamide, 3% Michael adduct and 10% water. After drying over $MgSO_4$ and repeated irradiation with a microwave power of 100 W for one minute, N-(triazolyl)methacrylamide was obtained with more than 98% purity and an APHA color number of 53.

Example 5

Preparation of
N-((pyridin-4-yl)methyl)methacrylamide 1 g of 4-aminopyridine was cooled while 2 molar equivalents of methacrylic acid were added and mixed in. After the exothermicity had abated, the ammonium salt thus obtained was exposed to a microwave power of 100 W in a closed cuvette with maximum cooling power within 2.5 minutes. In the course of this, the temperature rose to about 180° C., and the pressure gradually to 20 bar. Subsequently, the mixture was cooled to below 50° C. by air cooling within two minutes.

In the crude product, 81% of the 4-aminopyridine used had been converted to N-((pyridin-4-yl)methyl)methacrylamide. The further constituents of the crude product were water of reaction and unconverted reactants. After removal of the water of reaction, repeated microwave irradiation over 2 minutes and distillative removal of excess methacrylic acid and water of reaction, 98% N-(p-[N,N-dimethylamino]phenylene)-methacrylamide with an APHA color number of 62 was obtained.

Example 6

Continuous preparation of
N-(3-(N,N-dimethylamino)-propyl)methacrylamide 100 g of N,N-dimethylaminopropylamine were dissolved in 100 g of xylene with cooling and stirring and admixed slowly with an equimolar amount of methacrylic acid based on the amine. Once the exothermicity had abated the ammonium salt thus obtained was pumped continuously via the base inlet through the glass cuvette mounted in the microwave cavity. The delivery output of the pump was adjusted such that the residence time in the cuvette and hence in the irradiation zone was about 50 seconds. A microwave power of 200 W was employed with maximum cooling power, and a temperature of 150° C. measured by means of an IR sensor was attained. After leaving the glass cuvette, the reaction mixture was cooled to 30° C. by means of a short Liebig condenser.

The resulting crude product contained, as main components, 80% N-(3-(N,N-dimethylamino)propyl)methacrylamide, 7% Michael adduct, 8% water and unconverted reactants. After the reaction mixture had been dried over $MgSO_4$ and passed through the above process again and dried again, N-(3-(N,N-dimethylamino)propyl)methacrylamide with more than 98% purity was obtained. The APHA color number was 23.

Example 7

Continuous preparation of
N-(3-N,N-dimethylamino)propyl)-methacrylamide

A 50% solution of the ammonium salt of methacrylic acid and dimethylaminopropylamine (equimolar mixture, stabilized with 200 ppm of phenothiazine) in toluene was pumped continuously through the glass cuvette mounted in the microwave cavity. The delivery output of the pump was adjusted such that the residence time in the cuvette and hence in the irradiation zone was about 5 minutes. The microwave power was regulated between 25 W and 150 W such that, with maximum cooling power, a temperature between 150 and 160° C. measured by means of an IR sensor was maintained. After leaving the glass cuvette, the reaction mixture was cooled to 30° C.

The resulting crude product contained, as main components, 84% N-(3-(N,N-dimethylamino)propyl)methacrylamide, 2% Michael adduct, 9% water and unconverted reactants. After the reaction mixture had been dried over MgSO$_4$ and passed again through the above process and dried again, N-(3-(N,N-dimethylamino)propyl)methacrylamide was obtained with more than 98% purity. The APHA color number was 27.

Example 8

Continuous preparation of N-(3-N,N-dimethylamino)propyl)-methacrylamide

A 50% solution of the ammonium salt of methacrylic acid and dimethylaminopropylamine (equimolar mixture, stabilized with 200 ppm of phenothiazine) in toluene was pumped continuously through the glass cuvette mounted in the microwave cavity. The delivery output of the pump was adjusted such that the residence time in the cuvette and hence in the irradiation zone was about 2 minutes. The microwave power was regulated between 25 W and 200 W such that, with maximum cooling power, a temperature between 175 and 185° C. measured by means of an IR sensor was maintained. After leaving the glass cuvette, the reaction mixture was cooled to 30° C.

The resulting crude product contained, as main components, 85% N-(3-(N,N-dimethylamino)propyl)methacrylamide, 1% Michael adduct, 9% water and unconverted reactants. After the reaction mixture had been dried over MgSO$_4$ and passed again through the above process and dried again, N-(3-(N,N-dimethylamino)propyl)methacrylamide was obtained with more than 98% purity. The APHA color number was 17.

Examples 9 and 10

Continuous Thermal Reaction of Methacrylic Acid with Dimethylaminopropylamine

Comparative Examples

Analogously to examples 7 and 8, a 50% solution of the ammonium salt of methacrylic acid and dimethylaminopropylamine (equimolar mixture, stabilized with 200 ppm of phenothiazine) in toluene was pumped continuously through the pressure-resistant glass cuvette present in a sand bath at 300° C. The delivery output of the pump was adjusted such that the residence time of the reactants in the cuvette and hence in the heating zone was about 2 or 5 minutes. The temperature of the reaction mixture was measured at the outlet of the cuvette. The maximum temperatures observed here were 150 and 180° C. (see table below). After leaving the glass cuvette, the reaction mixture was cooled rapidly to room temperature.

The experiments led to the following results.

| Example | Residence time [min.] | Temperature | Amide [%] | Michael adduct [%] | APHA color number |
|---|---|---|---|---|---|
| 9 | 5 | 150° C. | 15 | 55 | 253 |
| 10 | 2 | 180° C. | 14 | 62 | 269 |

The fractions remaining to 100% are accounted for essentially by unconverted reactants, water of reaction and further unidentified by-products.

After the experiment, the reactor had solid brown deposits on the walls and the base, which indicate polymer formation and decomposition.

In order to study differences between the basic acrylamides prepared in accordance with the invention and corresponding basic acrylamides prepared conventionally by reacting methyl acrylate with dimethylaminopropylamine, both products were used for the preparation of high molecular weight copolymers with acrylamide. The copolymers thus prepared were then tested for their suitability as flocculation assistants.

Examples 11 and 12

Copolymerization of N-(3-(N,N-dimethylamino)propyl)acrylamide (DiMAPAM) with acrylamide In an insulated polymerization vessel, the amounts specified in table 1 of monomers and ABAH (2,2'-azobis-amidinopropane)dihydrochloride), and also bis(2-aminoethyl)amine-N,N,N',N'',N''-pentacetic acid, were dissolved in the amount of water specified. The reaction mixture was cooled to 10° C. with ice and, at the same time, inertized by passing nitrogen through for 90 minutes. Subsequently, tert-butyl hydroperoxide and, a further 5 minutes later, the pyrosulfite solution were added. A temperature rise indicated the onset of polymerization. Once the temperature maximum had been exceeded, the polymer was allowed to react to completion at 70° C. for approx. 12 h. The resulting polymer gel was comminuted, dried and ground.

TABLE 1

Reaction mixtures for polymerizations

|  | Example 11 Polymer A | Example 12 (comparative) Polymer B |
|---|---|---|
| Drinking water | 1500 g | 1500 g |
| Acrylamide | 350 g | 350 g |
| DiMAPAM (according to example 6) | 350 g | 0 g |
| DiMAPAM (conventional) | 0 g | 350 g |
| bis(2-aminoethyl)amine-N,N,N',N'',N''-pentacetic acid | 0.5 g | 0.5 g |
| 0.5% tert-butyl hydroperoxide | 5 g | 5 g |
| 0.5% sodium pyrosulfite | 5 g | 5 g |
| ABAH | 1.75 g | 1.75 g |

The relative viscosity (according to Ubbelohde at 25° C.) of 0.2% solutions of the two polymers in water was determined:

|  | Relative viscosity |
|---|---|
| Polymer A | 76.6 |
| Polymer B (comparative) | 66.1 |

Polymer A, prepared using N-(3-(N,N-dimethylamino)propyl)acrylamide prepared in accordance with the invention, leads, in an identical process regime, to a copolymer with significantly higher viscosity than comparative polymer B, which indicates a higher molecular weight of polymer A.

Example 13

Suitability of polymers of N-(3-(N,N-dimethylamino)propyl)acrylamide as a flocculation assistants In the winning of various minerals, the raw materials obtained as aqueous suspensions have to be dewatered. Among other things, very rapid sedimentation of the particles suspended in water is desired. To this end, polymers A and B were compared in a flocculation test in order to assess the speed of flocculation and especially the sedimentation of a mineral suspension.

Polymer A and polymer B were made up as 0.1% by weight stock solutions in tap water from 12 to 24 hours before the start of the test. To this end, 500 mg of polymer were stirred in 49.5 g of water in a closable sample vessel at room temperature with a magnetic stirrer bar for approx. 4 hours.

In a 2 l beaker, 1 l of a suspension comprising of 4% by weight of kaolin in tap water with various concentrations of the polymer A or B to be tested as a flocculant was stirred at approx. 1000 rpm for 15 seconds. Directly after the stirring, the suspension was transferred to a 1 l measuring cylinder. The sedimentation rate was determined by measuring the time needed for the boundary between clear supernatant and the kaolin suspension to cover the distance between two marks at a depth of 3 cm and 8 cm. The sedimentation rate is reported in cm/min. The results of the measurements are compiled in table 2:

TABLE 2

Sedimentation rate of additivized kaolin suspensions

| Test substance | Sedimentation rate [cm/min] | | | |
| --- | --- | --- | --- | --- |
|  | @5 mg/l | @7.5 mg/l | @10 mg/l | @15 mg/l |
| Polymer A | 11.8 | 17.2 | 23.5 | 37.1 |
| Polymer B (comp.) | 9.8 | 14.7 | 19.3 | 31.3 |

For each test concentration tested, the test results show more rapid sedimentation of the suspension treated with polymer A compared to that treated with polymer B (comparative).

These tests show that polymers with superior performance properties are obtainable through the use of monomers prepared in accordance with the invention.

The invention claimed is:

1. A process for preparing a basic amide of an ethylenically unsaturated C3- to C6-carboxylic acid, where the unsaturation is between the alpha and beta carbons of the carboxylic acid, by reacting at least one amine which contains at least one primary and/or secondary amino group and at least one tertiary amino group with at least one ethylenically unsaturated C3- to C6-carboxylic acid to give an ammonium salt, and subsequently converting the ammonium salt to the basic amide or imide under microwave irradiation, with the proviso that the primary and/or secondary amino group does not comprise any alkoxy groups.

2. The process as claimed in claim 1, wherein the at least one amine corresponds to the formula $HNR^1$-$(A)_n$-$Z$ wherein
$R^1$ is hydrogen, $C_1$-$C_{12}$-alkyl, $C_5$-$C_{12}$-cycloalkyl, $C_6$-$C_{12}$-aryl, $C_7$-$C_{12}$ aralkyl or a heteroaromatic group having from 5 to 12 ring members,
A is an alkylene radical having from 1 to 12 carbon atoms, a cycloalkylene radical having from 5 to 12 ring members, an arylene radical having from 6 to 12 ring members or a heteroarylene radical having from 5 to 12 ring members,
n is 0 or 1,
Z is a group of the formula —$NR^2R^3$ or a nitrogen-containing cyclic hydrocarbon radical having at least 5 ring members and
$R^2$ and $R^3$ are each independently $C_1$- to $C_{20}$-hydrocarbon radicals or polyoxyalkylene radicals.

3. The process as claimed in claim 2, in which $R^1$ is hydrogen or methyl.

4. The process as claimed in claim 2, wherein A is a linear or branched alkylene radical having from 1 to 12 carbon atoms and n is 1.

5. The process as claimed in claim 2, wherein $R^2$ and $R^3$ are each independently aliphatic, aromatic and/or araliphatic hydrocarbon radicals having from 1 to 20 carbon atoms.

6. The process as claimed in claim 5, wherein $R^2$ and $R^3$ are each independently alkyl radicals having from 1 to 14 carbon atoms.

7. The process as claimed in claim 2, wherein $R^2$ and/or $R^3$ are each independently polyoxyalkylene radicals of the formula —$(B$—$O)_m$—$R^4$ wherein
B is a linear or branched $C_2$-$C_4$-alkylene radical,
m is from 1 to 100,
$R^4$ is hydrogen, an alkyl radical having from 1 to 20 carbon atoms, a cycloalkyl radical having from 5 to 12 ring atoms, an aryl radical having from 6 to 12 ring atoms, an aralkyl radical having from 7 to 30 ring atoms, a heteroaryl radical having from 5 to 12 ring atoms or a heteroaralkyl radical having from 6 to 12 carbon atoms.

8. The process as claimed in claim 2, wherein Z is a nitrogen-containing cyclic hydrocarbon radical whose nitrogen atom is incapable of forming amides.

9. The process as claimed in claim 1, wherein the at least one amine is selected from the group consisting of N,N-dimethylethylenediamine, N,N-dimethyl-1,3-propanediamine, N,N diethyl-1,3-propanediamine and N,N-dimethyl-2-methyl-1,3-propanediamine.

10. The process as claimed in claim 1, wherein the at least one ethylenically unsaturated carboxylic acid is selected from the group consisting of acrylic acid, methacrylic acid, crotonic acid, 2,2-dimethylacrylic acid, maleic acid, fumaric acid and itaconic acid.

11. The process as claimed in claim 1, wherein the microwave irradiation is performed in the presence of a dehydrating catalyst.

12. The process as claimed in claim 1, wherein the microwave irradiation is performed in the presence of a solvent.

13. The process as claimed in claim 12, wherein the solvent has a dielectric loss value of below 10.

14. The process as claimed in claim 1, wherein the microwave irradiation is performed at temperatures below 300° C.

15. The process as claimed in claim 1, wherein the reaction is performed at a pressure between 0.1 and 200 bar.

16. The process as claimed in claim 1, wherein the reaction is effected continuously by irradiating with microwaves in a reaction tube through which the ammonium salt flows.

17. The process as claimed in claim 16, wherein the reaction tube consists of a nonmetallic, microwave-transparent material.

18. The process as claimed in claim 16, wherein the residence time of the reaction mixture in the reaction tube is less than 30 minutes.

19. The process as claimed in claim 16, wherein the reaction tube has a ratio of length to diameter of at least 5.

* * * * *